(12) United States Patent
Senia et al.

(10) Patent No.: US 6,579,092 B1
(45) Date of Patent: *Jun. 17, 2003

(54) ENDODONTIC INSTRUMENTS WITH MEANS FOR BREAKAGE CONTAINMENT

(75) Inventors: Steve S. Senia, San Antonio, TX (US);
E. Steve Senia, San Antonio, TX (US);
William L. Wildey, Keller, TX (US)

(73) Assignee: Lightspeed Technology, Inc., San Antonio, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,729

(22) Filed: Dec. 7, 1999

Related U.S. Application Data (60) Provisional application No. 60/147,973, filed on Aug. 9, 1999.

(51) Int. Cl.⁷ .................................................. A61C 5/02
(52) U.S. Cl. ...................................................... 433/102
(58) Field of Search ............................... 433/102, 144, 433/147, 165, 166

(56) References Cited

U.S. PATENT DOCUMENTS

| | | | | |
|---|---|---|---|---|
| 993,100 A | * | 5/1911 | Powers | 433/147 |
| 2,334,755 A | * | 11/1943 | Eglinton | 433/165 |
| 2,861,341 A | * | 11/1958 | Bjorklund | 433/165 |
| 3,330,040 A | * | 7/1967 | Kahn | 433/102 |
| 3,670,416 A | * | 6/1972 | Kroder | 433/165 |
| 3,850,054 A | * | 11/1974 | Weissman | 433/165 |
| 3,906,636 A | * | 9/1975 | Rainey et al. | 433/165 |
| 4,609,352 A | * | 9/1986 | Riitano | 433/102 |
| 4,674,979 A | * | 6/1987 | Jacklich | 433/102 |
| 4,850,867 A | * | 7/1989 | Senia et al. | 433/102 |
| 5,380,200 A | * | 1/1995 | Heath et al. | 433/102 |
| 5,915,964 A | * | 6/1999 | Walia | 433/102 |
| 6,106,291 A | * | 8/2000 | Boston | 433/165 |

FOREIGN PATENT DOCUMENTS

| | | | | |
|---|---|---|---|---|
| DE | 2524105 | * | 1/1976 | 433/102 |

* cited by examiner

*Primary Examiner*—Todd E. Manahan
(74) *Attorney, Agent, or Firm*—Jackson Walker, L.L.P.

(57) ABSTRACT

An endodontic instrument having a shaft with a near end and a removed end. The shaft is comprised of a first material. A head, the head being comprised of a second material is attached to the removed and of the shaft. The shaft is rotated so as to move with the shaft. The head is permanently attached to the shaft. The head is typically shaped to allow for the cutting of dentin or other tooth or pulp material. Applicant also provides a method for manufacturing such an endodontic instrument by including the steps of forming a tooth cutting member such as a head, forming an elongated shaft and permanently attaching the tooth cutting member or head to the shaft.

9 Claims, 7 Drawing Sheets

ENDODONTIC INSTRUMENTS WITH MEANS FOR BREAKAGE CONTAINMENT

This application claims the benefit of provisional application No. 60/147,973 field Aug. 9, 1999.

BACKGROUND OF THE INVENTION

1. Field of the Invention

Endodontic instruments, more specifically: an instrument wherein the head and shaft are separately manufactured and then joined; wherein an instrument may have a shaft with a first composition and a head located at a removed end of the shaft, the head with a second composition; and an instrument with an integral retrieval means.

2. Background Information

Endodontic instruments are used to clean and shape a root canal, for subsequent filling. Prior art endodontic instruments are typically made from the same material and in a single step as an integral unit with an elongated working member having a cutting portion for cutting the canal and a non-cutting portion for insertion into a handle. A handle which is attached to the first or near end of the shaft is rotated while the instrument is inserted into the canal where the rotation of the cutting head or cutting portion against the walls of the tooth canal effects a reaming or cleaning of the canal.

Applicant provides a number of improvements in prior art endodontic instruments and irrigating devices. First, Applicant provides an endodontic instrument with a working portion created by the joiner of a separate shaft (non-cutting portion) and a separate head (cutting portion). This is provided in place of the prior art teaching of a unitary working member with a cutting portion at one end thereof. Applicant's endodontic instrument provides for a number of advantages over the prior art as set forth more fully below.

Further Applicant provides an endodontic instrument including means for retaining a shaft on the instrument if the shaft were to break.

Further, Applicant provides an endodontic instrument with a friction grip handle for engagement with a drive tool.

Further, Applicant provides for a unique device, for injecting and agitating irrigation fluid into the root canal system.

The purpose of the shaft is to locate the head of the instrument into the canal and bring it back. Further, the shaft is used to drive the head. In the past, materials of the one piece head and shaft were the same (typically metal) so you could not optimize head and shaft requirements. While the shaft should be flexible to keep the head centered in the canal and be capable of bringing the head into and out of the canal, the head of the shaft should be an effective cutting agent shaped and made of a material that will promptly and effectively cut the canal walls.

Applicant provides for an endodontic instrument in which a shaft and head are manufactured separately, then joined together, with typically, a handle attached to the shaft on the end opposite the head. The shaft and the head may be manufactured from the same material or from different material.

In the past, the shaft and head were an integral member made of the same composition; that is, stainless steel, nickel titanium, etc. Applicant also provides a novel device with two or more different materials; a shaft of a first composition (optimally flexible and durable) and the head of a second composition (optimally hard and shaped with cutting edges) for effectively cutting tooth canal material.

The function of the head is to cut, clean, and stay centered in the canal and remove the abraded material. This is best performed by materials whose properties are different than the function of the shaft, which should be flexible, durable, and capable of placing a head into and out of a root canal.

Breakage of an instrument in a canal creates obvious problems. Prior art methods for avoiding such problems are, in the main, preventative, including keeping a close track of the number of times that the instrument has been used so its use may be discontinued after a number of uses. Therefore, it is clear that an instrument that is capable of being retrieved if broken would provide a greater utility to the dentist.

Rotary endodontic instruments typically rotate rapidly and flex while the dentist is shaping and cleaning within the root canal. The repeated flexing causes them to, ultimately, fail by breaking, usually along the shaft between the handle and the head of the instrument. If the breakage occurs during use, the dentist is faced with the often formidable task of recovering the broken pieces or leaving the broken pieces in the tooth.

Applicant provides a solution to the breakage problem by focusing on the retrieval of the broken pieces of the instrument. By providing structural means to retrieve the broken pieces from the tooth, Applicant's endodontic instrument may be made or constructed with a shaft of stainless steel, nickel-titanium or any other suitable material. The breakage of a shaft becomes less of a concern to the dental professional when structural means are provided that will provide a retrieval mechanism.

When breakage of the instrument occurs inside the tooth the broken pieces of the instrument should be removed. An invention which has a built-in retrieval device clearly has advantages in such a situation. Applicant provides in the following description and claims a design for such an instrument.

It is an object of the present invention to provide an endodontic instrument which optimizes advantageous properties of a head made of a first composition and optimizes advantageous properties of a shaft made of a second composition.

It is another object of the present invention to provide an endodontic instrument, such as a drill with a built-in, broken tool retrieval device.

This and other objects are provided for in an invention set forth below and described with reference to the attached figures.

Applicant also provides yet another unique endodontic instrument for cleaning a tooth canal and a method for manufacturing the same. This instrument includes a separate shaft to which a separate head is joined. Applicant's novelty lies in providing for manufacturing the shaft separate and apart from the head and, following the manufacturing the head and shaft separately then joining the two. This provides for advantages including optimizing the performance of the two individual components. It is noted in this embodiment of this applicant's invention that the separate manufacturing steps of manufacturing the shaft and the head may be provided wherein the shaft and head material are of the same composition or wherein the shaft and head material are different compositions.

In the first instance, for example, the shaft and head may be made from stainless steel, nickel titanium, plastic or the like. The shaft is manufactured and fashioned as an elongated typically cylindrical, hollow tube or solid wire, coil wound section, or a series of gears, or wire mesh with the head manufactured separately in a manner and shaped for efficient cutting and cleaning. The pieces are then joined as by bonding, welding, gluing, etc. (method of joining).

On the other hand, a shaft may be made as set forth above and a head may be provided of a different material as such as those materials set forth above and then the shaft and the head joined. It is noted that the separate manufacturing steps of manufacturing the two pieces (shaft and head) apart from one another allows the instrument designer greater variation in the dimensions and shape of the individual piece then the prior art method which shapes the shaft and the head as an integral piece in the single manufacturing process. That is, in the prior art a blank was provided from which an integral head and shaft unit is tooled.

SUMMARY OF THE INVENTION

Applicant's provide for this and other objects by providing a rotatable endodontic instrument having a handle for attachment to a shaft, the shaft with a near end and a removed end, the handle at the near end thereof and a head, cooperating with the shaft at the removed end of shaft so as to rotate therewith. Applicant further provides for a sleeve, dimensioned for receipt over the shaft, to substantially enclose the shaft between the handle and the head of the shaft, with the sleeve and the shaft being glued, soldered or otherwise attached to one another. Therefore, if breakage of the shaft occurs the sleeve still maintains its integrity and will substantially enclose the broken piece, typically preventing it from escape from the instrument and remaining in the canal.

Applicant further provides for this and other objects and purposes in providing an endodontic instrument which includes a shaft, the shaft enclosed by a coil spring and attached to the coil spring such that both the shaft and the coil spring rotate together. At one end of the shaft is a head and at the other end of the shaft is a handle. Rapid rotation by the handle allows the head to do its cutting work on the tooth. However, should the shaft break the coil spring will retain, within the coil, the broken piece.

BRIEF DESCRIPTION OF THE PREFERRED EMBODIMENT

DETAILED DESCRIPTION OF THE PREFERRED EMBODIMENTS

FIGS. 1, 1A, 2 and 3 represent an endodontic 10 instrument comprised of three parts: a head 12 attached to the removed end of a shaft 14, the near end of the shaft having a handle 16. Optionally, the handle may have a latch indent 18 for attachment of the handle to a dental hand piece.

Figure 1:
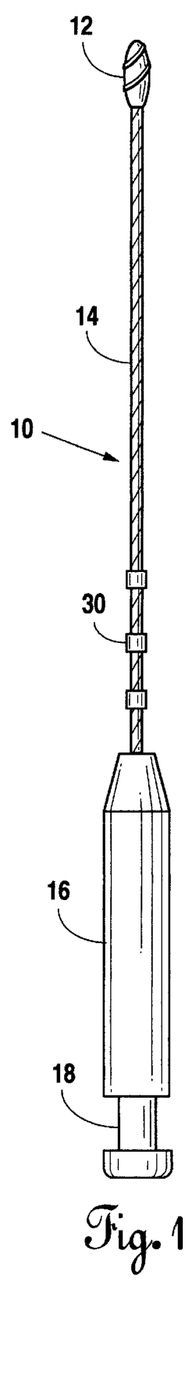
FIG. 1 is a side elevational view of the three piece endodontic instrument having a handle, shaft and head, the shaft being made of coiled metal wire.
Figure 1A:
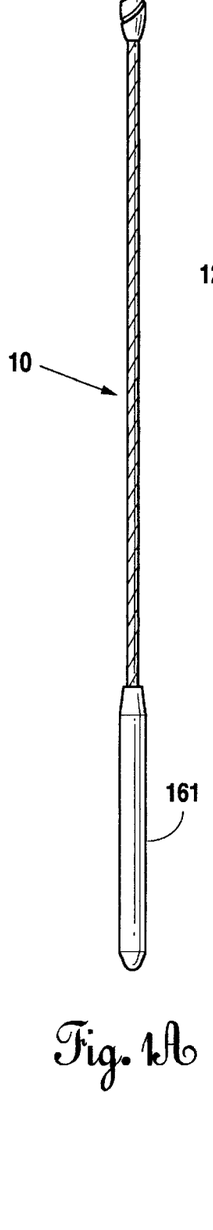
FIG. 1A is a side elevational view of the endodontic instrument of FIG. 1 but with a handle adopted to accept a friction grip mechanism.
Figure 2:
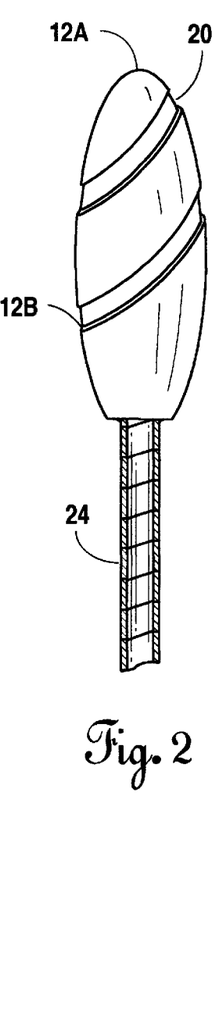
FIG. 2 is a partial side elevational view of the FIG. 1 is a side elevational view of the three piece endodontic instrument having a handle, shaft and head, the shaft being made of coil metal wire.
Figure 3:
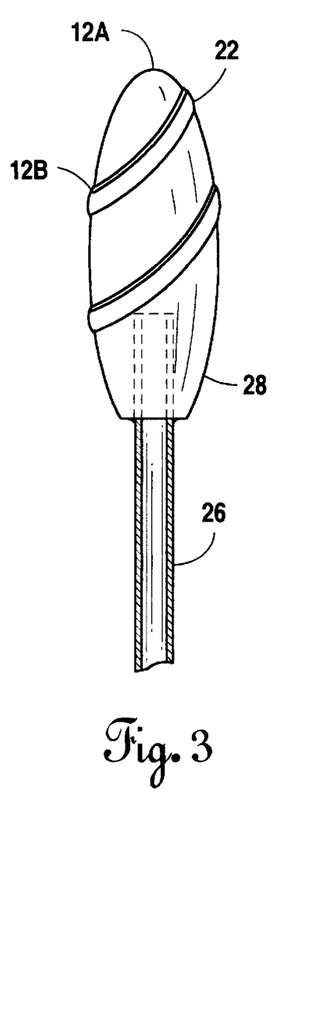
FIG. 3 is a partial side elevational view of the endodontic instrument showing a tubular shaft for receipt of a separate head thereinto, the head having ridges as cutting elements instead of grooves.

The two handles in FIGS. 1 and 1A differ in that in FIG. 1 there is a latch indent 18 in the handle, and in FIG. 1A, handle 161 has a narrower diameter and is designed to be accepted in a friction grip mechanism of a drilling device, such as those manufactured by NSK. Applicants novel friction grip handle is smaller in diameter (typically less than about 4 mm and preferably about 1.6 mm and shorter in length typically between 5 and 20 mm and preferably 10 to 11 mm) and does not require alignment with a drive tool as does handle illustrated in FIG. 1. Any other type of suitable handle may be used. The handle may be made out of aluminum, brass, plastic, stainless steel, etc.

The cutting head 12 may be of any hard, durable material shaped with flutes or grooves 20 (see FIG. 2), ridges 22 (see FIG. 3), or other suitable shapes. Heads may be ground by a machinist using a five axis grinding machine such as one available from Unison®. They may be solid or hollow.

Figure 13:
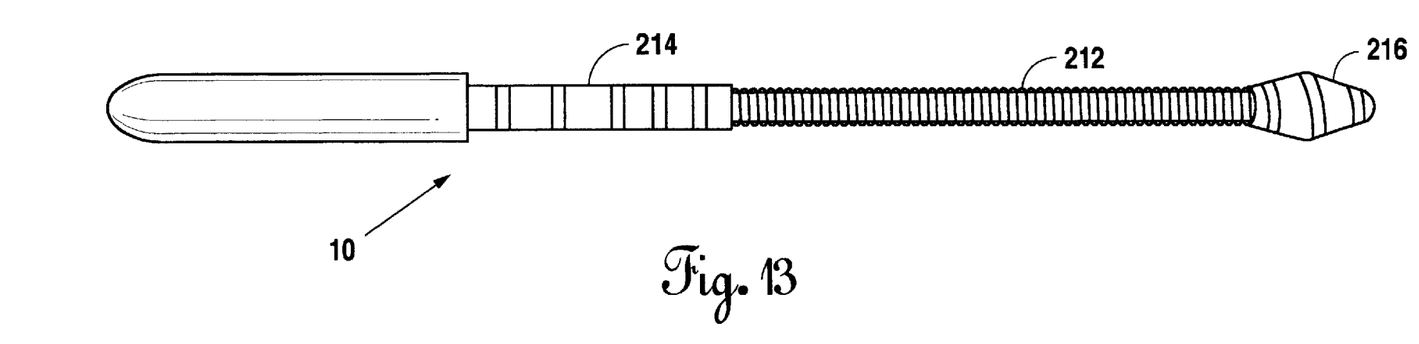
FIG. 13 illustrates yet another alternate preferred embodiment of Applicant's present invention, here featuring a shaft of a tightly coiled spring.
Figure 14:
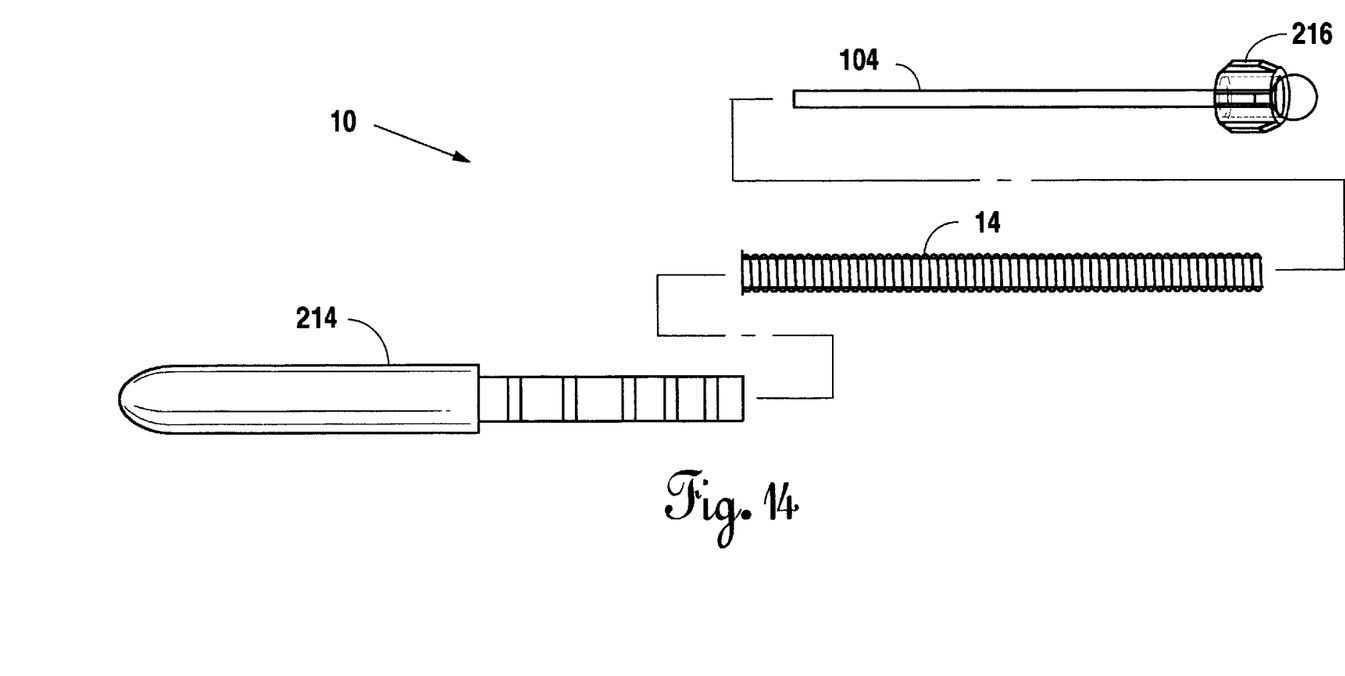
FIG. 14 illustrates yet another alternate preferred embodiment of Applicant's present invention, here featuring a retainer wire enclosed within the shaft.

Turning now to the shaft, the shaft 14 may be made of any flexible, durable material, such as metal (for example stainless steel or nickel-titanium), plastic, rubber, carbon fiber, composites, or the like. Further, the shaft may be hollow, solid, or may be formed from a coil spring 24 (see FIGS. 1, 1A, and 2), braided wire mesh or a series of small gears. Hollow tubular or solid stock from which shafts may be made are available from a stock from a number of suppliers. See FIGS. 10B, 11, 13 and 14 for illustrations of variations of Applicants drive shafts, including gear (FIG. 10B), wire mesh (FIG. 11), tightly wound wire coils (FIGS. 13 and 14). Depth gauge 30 (or any measuring rings or other means) may be provided along the shaft or handle to allow the dentist a means of determining the depth of the instrument in the canal.

The shape of the head 12 is noted to have a rounded or pointed nose 12A, which is helpful to accomplish the centering purposes of the instrument. However, the shape of the head may be any suitable shape. Second, the surface of the head is seen to contain cutting edges, here either grooves 20 or Applicant's novel ridges 22. Grooves or ridges may take a spiral shape with a longitudinal axis of the instrument which allows for both effective cutting and shunting of the cut debris towards the canal's orifice (towards the handle). Both the grooves and the ridges typically have edges 12B which will cut into the canal wall when the head is urged into the tooth. The ridges may be formed from diamonds layered over the body of the head, bonded to the head by electromechanical galvanic gluing or other ways known in the trade.

The head is made of a hard material, meaning a material that will cut dentin within the tooth, and may itself be composed of one or more materials, such as metal (for example, stainless steel and nickel titanium), ceramic, diamond, or other mineral, rubber, composites, carbon fiber, or anything else that is hard. On the other hand, the shaft should be flexible and durable and is not required to have all of the same properties of the head.

Figure 4:
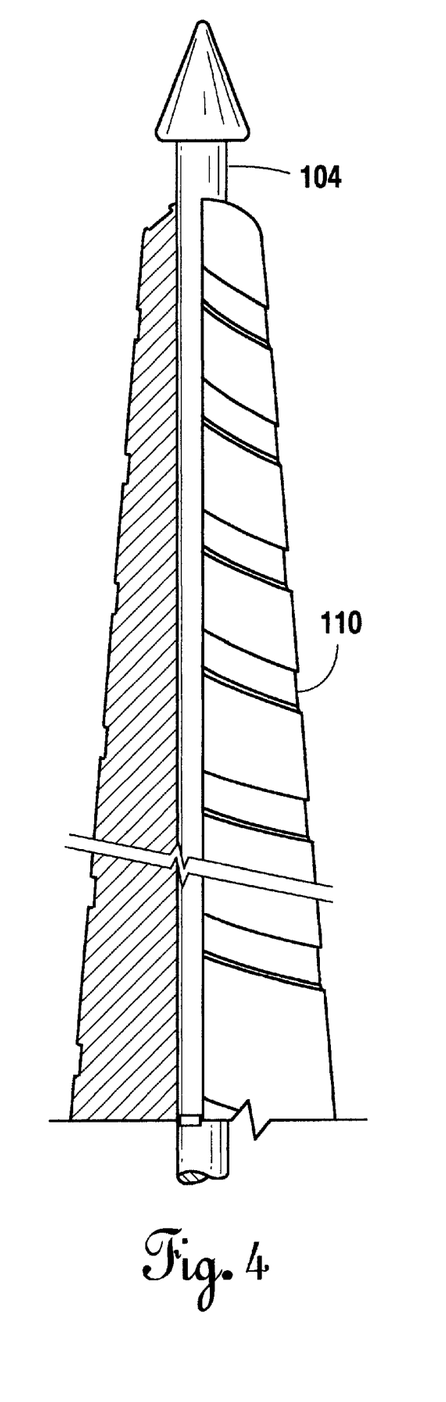
FIGS. 4 and 5 are side elevational, partially cutaway views of a removed end of an alternate preferred embodiment of Applicant's endodontic instrument.
Figure 5:
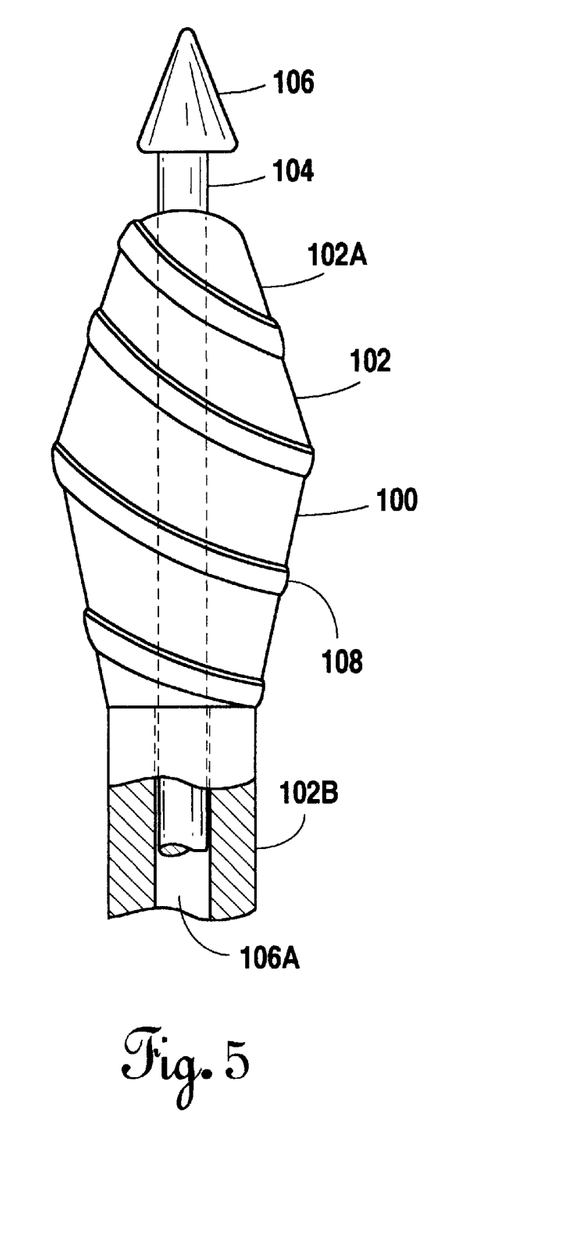

Turning now to FIGS. 4 and 5, it is seen that Applicant provides an endodontic instrument with a removed end 100 having a rotating cutting member or head 102, which rotating cutting member includes a cutting portion 102A and a non-cutting portion 102B. It is noted that the cutting portion has grooves or ridges with cutting edges thereon, and may be spiraled such that it may cut dentin (being harder than the tooth material) and, with the spiral shape, may transmit the cut debris along the longitudinal axis of the instrument away from the head. However, it is seen that the rotating cutting member has a longitudinal axis and, further, a longitudinal bore 106A and rides on a retainer wire 104. Moreover, at the removed end of the retainer wire, distal to the end of the cutting portion of the rotating member, is found a stop member 106, here cone-shaped (or may be circular or rounded or any other suitable shape), where the base of the cone has a diameter greater than the uniform diameter of the retainer wire 104. Therefore, if a break occurs, as at A in FIG. 4,(or anywhere along the shaft that rotates member 102) and the rotating member 102 now is in two pieces instead of a single piece, the effect of having the retainer wire 104 will be to prevent the loss of the broken piece of rotating member 102. That is, if the head or shaft breaks then the shaft 104 is simply removed from the canal carrying with it the broken rotating member on retaining wire 104. The retainer wire is separate from the shaft and the head and may or may not be attached to the handle.

It can be appreciated that there may be potentially serious consequences leaving a broken fragment in the operation of cleaning the canal. It may be avoided by providing the retrieval device as designed.

FIGS. 6–9 illustrate additional embodiments of Applicant's endodontic instrument 10. As appreciated with reference to FIG. 6, Applicant's endodontic instrument 10 includes a shaft 14 having a removed end 14A, a body 14B and a near end 14C. The shaft is typically cylindrical and typically dimensioned between 0.001 millimeter and 2.0 millimeters in thickness and is typically 1.0 millimeter to 100 millimeters in length. The shaft may be made from nickel-titanium, stainless steel, plastic or any other suitable material.

Figure 6:
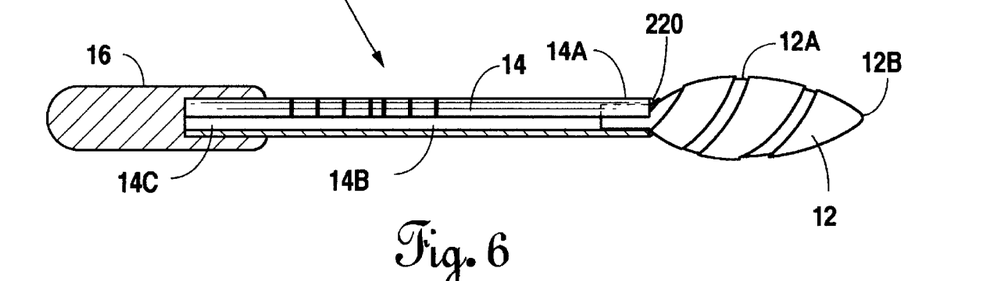
FIGS. 6 and 6A are a side elevational view of Applicant's endodontic instrument without the sleeve.

At the near end 14C of Applicant's shaft 14 and joined thereto is a handle 16, which may either be for engagement with a friction grip or a latch handle for engagement with a motor drive. The handle is typically cylindrical and made of aluminum, brass, plastic, or any other suitable material.

Figure 6A:
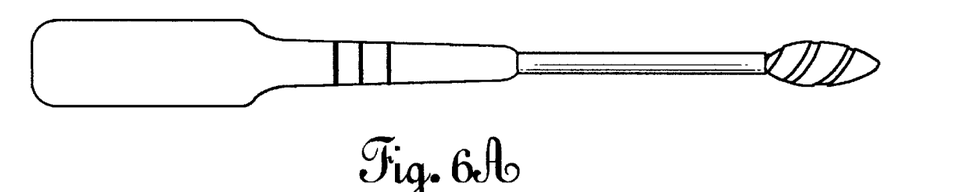

At the removed end 14A of Applicant's shaft is a head 12, the head having cutting blades or cutting means 12A thereon and, optionally, having a cutting or non-cutting pilot portion 12B thereon. The head may be formed from the same material as the shaft or from a different material such as: stainless steel, nickel titanium, carbide steel or any other suitable material. FIG. 6 shows the use of depth gauges or rings 30 along the shaft whereas FIG. 6A shows them along a narrow section of the handle.

In FIGS. 7, 8, 15 and 16 applicant provides a novel sleeve 218 dimensioned for snug receipt over the shaft and extending from the base of the cutting head at the removed end of the shaft to the near end of the shaft. The sleeve may be a coil spring, tightly coiled with little or no space between the adjacent throws of the coil, and typically made of stainless steel or other suitable biocompatible material. The sleeve, typically being a coil spring, may bend or flex and is attached to the shaft near the head or to the head itself so as to rotate therewith. Attachment by mechanical or adhesive means 220 such as by welding, gluing or soldering may be made, typically near the point near where the head joins the sleeve.

The purpose of the coil spring sleeve is to allow the shaft to flex but if the shaft breaks, to contain within the coils of the coil spring the broken pieces. This allows the pieces to be retrieved from the tooth. Applicants testing has indicated that springs made of small diameter stainless steel wire will exceed the breakage life cycle of the shaft. In other words, because the shaft will break well before the spring and because the shaft and spring are joined a least near the removed end thereof, any breakage along the shaft as a result of continued flexing and rotating will be contained within the coil spring.

Figures 7, 8, 9:
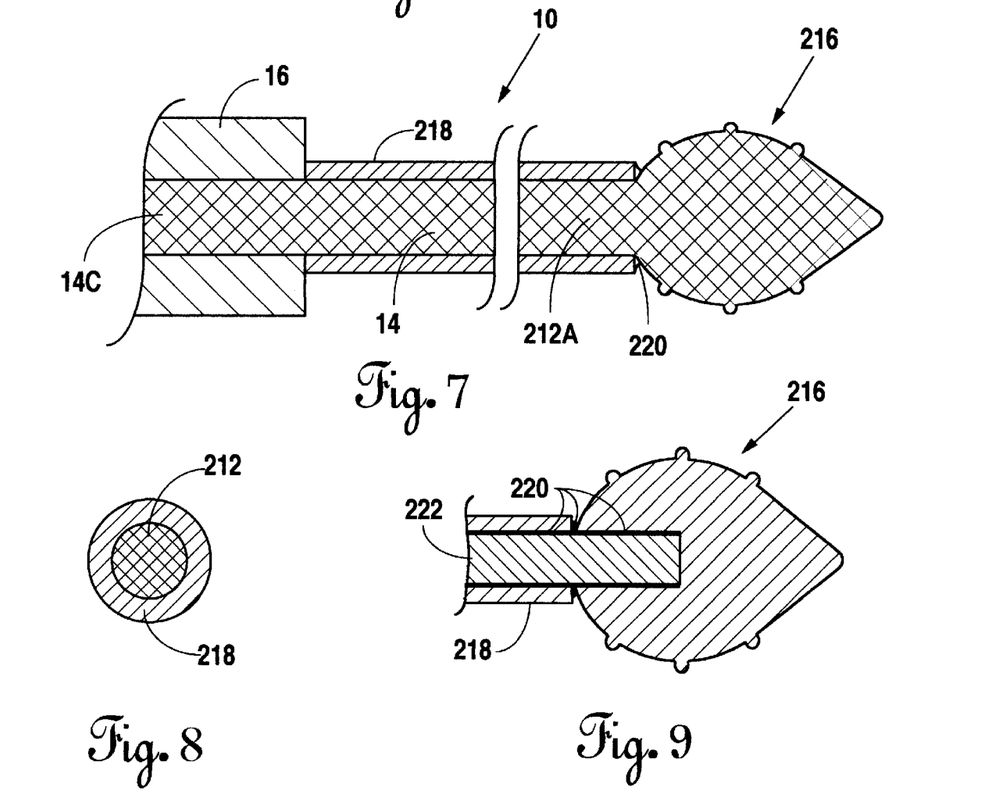
FIG. 7 is a side elevational view (cut away) of Applicant's endodontic instrument.
FIG. 8 is a cross sectional view perpendicular to the longitudinal axis of Applicant's present invention between the near and removed end of the shaft.
FIG. 9 is a partial view of Applicant's endodontic instrument parallel to the longitudinal axis, the removed end, sleeve and head of Applicant's endodontic instrument.

FIG. 7 shows use of a solid shaft 14, FIG. 6 shows a hollow tube shaft 14, both may be covered by the coil spring sleeve. FIG. 7 shows the head integral with the shaft but they may be two separate parts (as in FIG. 6, 220 being an adhesive or weld).

FIG. 8 is a cross section through the body of the endodontic instrument of FIG. 7 showing the sleeve over a solid shaft.

FIG. 9 shows the coil spring sleeve with adhesive 220 holding the head to the shaft and sleeve to the shaft near the head.

Because the sleeve is typically attached to the shaft only near the head and further, because in this embodiment the sleeve is not attached to the rotating handle (which turns the shaft), when the shaft, breaks the head and the sleeve portion proximal to the break will stop rotating and the dentist can slide the proximal (still spinning) shaft from the sleeve and retrieves the sleeve and broken section of the shaft and the head by grasping the sleeve at its proximal end with an appropriate tool.

Figure 10A:
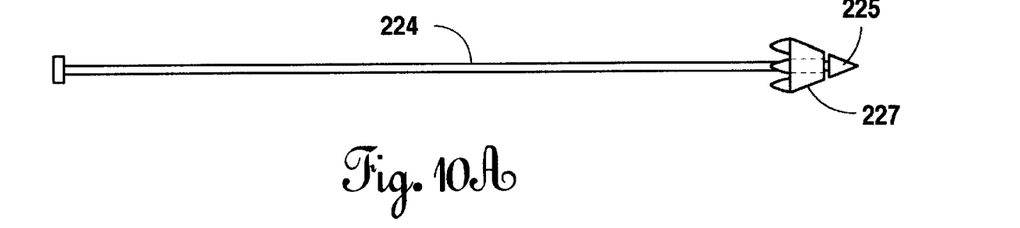
FIGS. 10A, B, and C illustrate yet another alternate preferred embodiment of Applicant's present invention.
Figure 10B:
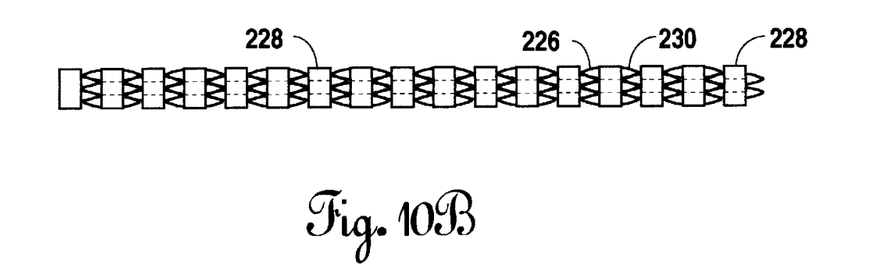
Figure 10C:
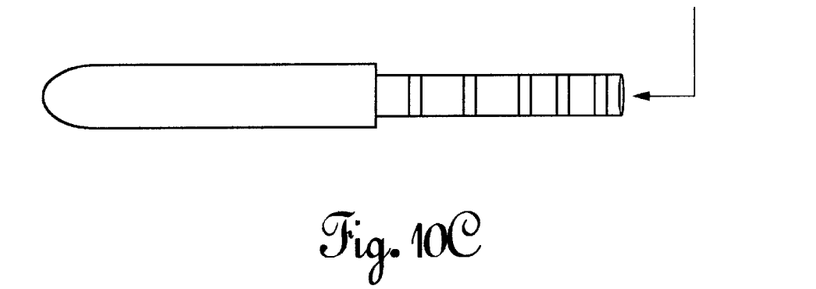

FIGS. 10A–C illustrates an additional embodiment of the retainer wire here, a centrally located retainer wire 224 where the retainer wire may be stationary (or may rotate) with a boss 225 on the distal end holding the cutting head 227 in place. Here, a shaft 226 (FIG. 10B) is shown made up of a series of similarly shaped, discrete gears 228, strung along the retainer wire and held between the boss and the proximal end of the retainer wire. Use of the multiplicity of separate gears with interlocking teeth 230 should prevent the shaft from breaking apart as the gears will likely "strip" before breaking since they are driving the head but will not fall off due to the retainer wire. Further, use of this design will allow the shaft to easily flex without "stretching" the metal.

Figure 11:
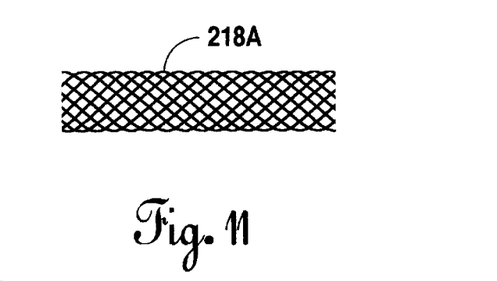
FIG. 11 illustrates yet another alternate preferred embodiment of Applicant's present invention, here featuring a mesh sleeve.

FIG. 11 illustrates a wire mesh sleeve 218A made from fine wires woven together. This sleeve may be used in place of sleeve 218 in the embodiments illustrated in FIGS. 6 through 9.

Figure 12A:
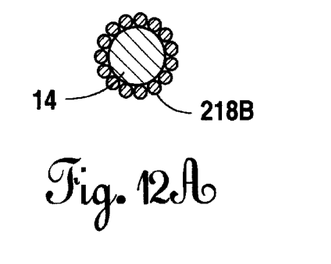
FIGS. 12A and 12B illustrate cutaway and side elevational views of yet another alternate preferred embodiment of Applicant's present invention featuring a shaft contained within round wire strands.
Figure 12B:
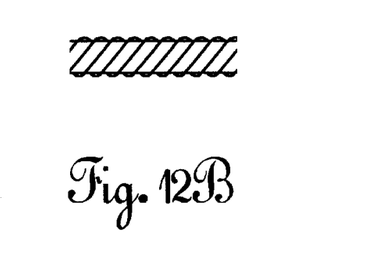

FIGS. 12A and 12B illustrate use of a solid shaft 14 with wires 218B around the exterior thereof for use in the embodiments illustrated in FIGS. 6 through 9 for providing a retrieval device for a broken shaft.

Yet another invention Applicant provides is an endodontic instrument and a method of making an endodontic instrument wherein the shaft of the endodontic instrument is not produced by grinding down to size. That is, prior art provides shafts for endodontic instruments and method for making the shaft wherein the shafts are reduced to an appropriate diameter by grinding the shaft. This causes small stress fractures and reduces the life cycle of the shaft. However, Applicant provides a drawn or molded shaft (for example see shaft 14 in FIG. 16) (or any other shaft except the shaft that is ground down) and therefore, provides in a shaft a method for making a shaft of an endodontic instrument which has greater life cycle than those currently available and those provided in the prior art.

FIG. 13 provides yet another embodiment of Applicant's endodontic instrument 10. This embodiment uses a tightly coiled spring as shaft 212, the coil spring attached to and used for rotating head 216. Coil spring shaft 212 is attached to handle 214 and a head 216, causing the head to spin. Coil winding, either single or multi-filar coil windings may be stainless steel, MP35N, platinum, or many other alloys may be used for the shaft illustrated in FIG. 13 or the coil spring sleeve 218 illustrated in FIGS. 7, 8 and 9. Indeed, single or multi-filar coil windings can be used in the mesh windings illustrated in FIGS. 11, 12A and 12B. Such windings are available Star Guide Corporation, 5000 Independence Street, Arvada, Colo.

FIG. 14 illustrates yet another embodiment of Applicant's endodontic instrument 10. In this embodiment a coil wound shaft 14 is used, and attached to the handle and to a cutting head 216. This embodiment uses a retainer wire 104 and a coil wound drive shaft for driving a cutting head 216. Here, the retainer wire is enclosed within shaft 14. Shaft 14 is not attached to the retainer wire. Shaft 14 is attached to the handle and the cutting head and causes the cutting head to rotate. As in earlier embodiments, any breakage of the shaft 14 will be retained on retainer wire 104. Using a multi-filar shaft provides an instrument with a longer life than current instruments provided.

Figures 15, 16:
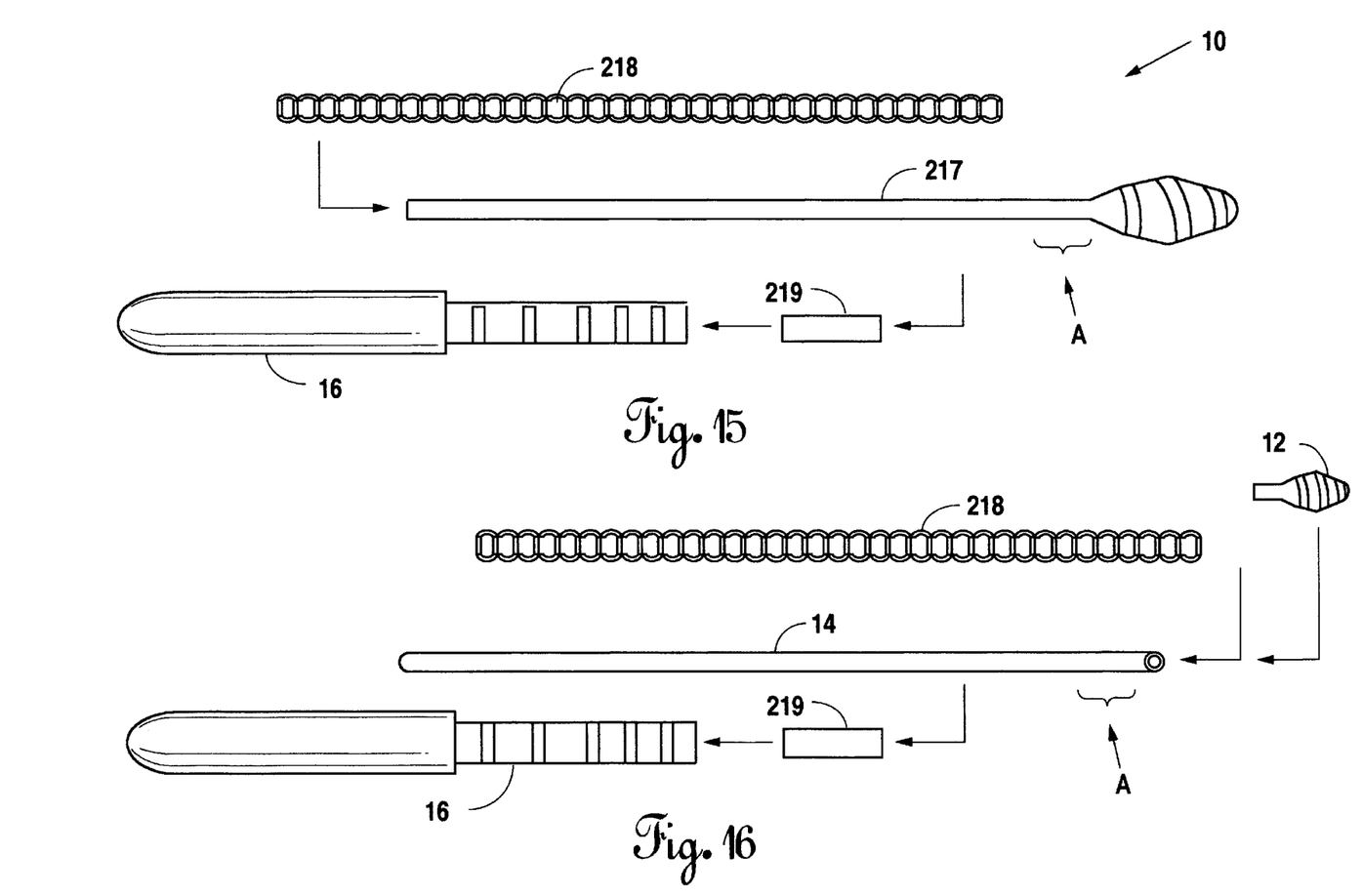
FIG. 15 illustrates yet another alternate preferred embodiment of Applicant's present invention, here featuring a unitary shaft/cutting head.
FIG. 16 illustrates yet another alternate preferred embodiment of Applicant's present invention, here featuring a tubular shaft.

FIG. 15 illustrates an endodontic instrument 10 which instrument has a unitary shaft/cutting head member 217. Optionally, a spacer 219 may be used where the near end of unitary cutting head shaft 217 inserts into handle 16 to fit the handle to the shaft. This one piece design may be used with sleeve 218 which may be made of single or a multi-filar coil winding from stainless steel, MP35N, platinum content and many other alloys. At "A" the sleeve is bonded, welded or otherwise attached to the shaft and head of member 217. Star Guide Corporation provides such sleeves in appropriate dimensions.

FIG. 16 illustrates the use of a tubular shaft 14 with head 12 inserted into the removed end. The tube may be nickel-titanium, stainless, plastic steel, fiberglass or any other suitable material. The sleeve will slide over the shaft and will be attached to the shaft near the cutting head (the cutting head being inserted here into the tubular shaft at the removed end). Welding, gluing or otherwise retaining the retrieving sleeve 218 to the shaft and only near the head of the shaft (at "A") any breakage in the shaft between the point of attachment and the handle will cause the sleeve to stop spinning. One can then remove the head and the sleeve from the tooth canal.

Figure 17:
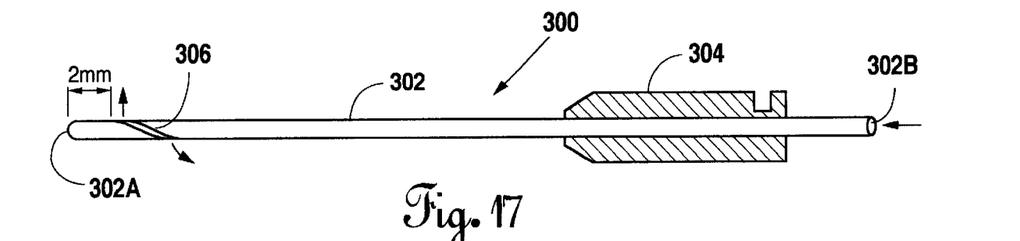
FIG. 17 illustrates yet another alternate preferred embodiment of Applicant's present invention, here featuring an integrated irrigating device.

In the process of doing root canal work the dentist is required to irrigate the work space. However, it is difficult to get the irrigating solution (typically bleach) into every crevice. Dentists now use syringes to force the irrigating solution out the tip of the syringe and into the root canal area. The solution is then suctioned back out. The dentists must be careful that they do not force the solution periapically which would cause pain to the patient. In FIGS. 17 through 20 applicant provides for an irrigating device 300 which includes a tube 302, the tube having a handle 304 at the removed end thereof. As can be seen as with reference to the attached figures tube 302 is hollow (FIGS. 17, 18 and 19) but has a closed removed end 302A and a hollow opening at near end 302B. Near the removed end 302 are high pressure slots or openings 306 which drive the high pressure irrigating solution out the tube laterally with respect to the long axis of the tube and not out the blocked tip. The reason applicant's device urges the irrigating fluid laterally is to decrease the possibility of pain to the patient. Holes 306 may be slots or have any other configuration necessary to drive high pressure fluid laterally with respect to tube 302. In FIG. 17 the tube is seen to extend through the handle. The irrigating device illustrated may be used with a reciprocating type handpiece.

Figure 18:
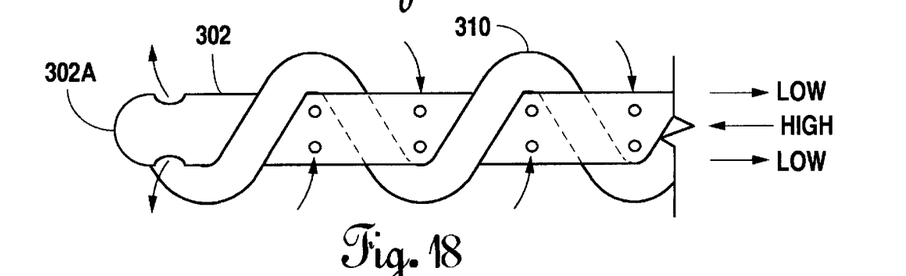
FIG. 18 illustrates yet another alternate preferred embodiment of Applicant's present invention, here featuring an irrigating device and illustrating solution flow.
Figure 19:
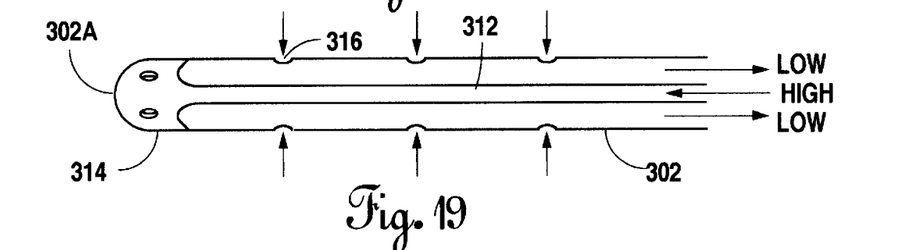
FIG. 19 illustrates yet another alternate preferred embodiment of Applicant's present invention, here featuring an irrigating device and illustrating solution flow.
Figure 20:
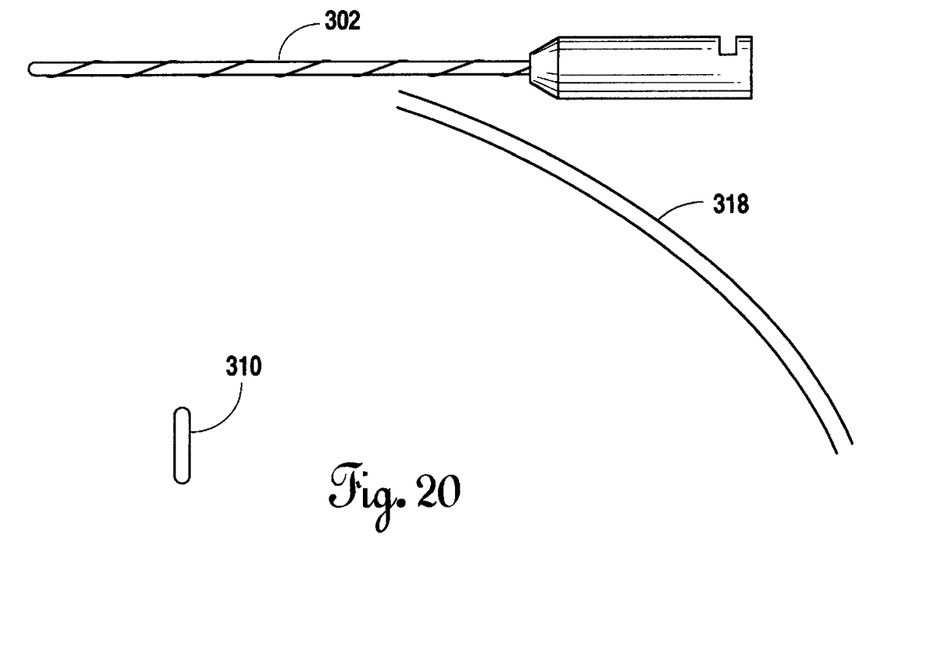
FIG. 20 illustrates yet another alternate preferred embodiment of Applicant's present invention, here featuring a separate irrigating device.

Irrigating device 300 is usually motor driven, reciprocating back and forth to insure proper agitation of the irrigating solution. Near end 302B may be attached to a source of high pressure irrigation solution or a source of high pressure irrigating solution which alternates with suction so that instrument 300 injects the irrigating solution into the tube and suctions it out. FIG. 18 illustrates how alternating high and low pressure in the tube may drive the fluid out of and into the tube. Ridges or non-cutting blades on the exterior of the tube are used for agitation of the solution much like a washing machine agitator. FIG. 19 illustrates a tube in which a high pressure inner tube 312 injects the irrigating fluid out distal located holes 314 while, simultaneously or alternatively, fluid is being suctioned back into the tube through low pressure holes 316. FIG. 20 illustrates a separate irrigating tube 318 for use in conjunction with a solid, bladed instrument tube 302 or flat blade and includes a cross-sectional view of non cutting blades 310 whose function is to agitate in the workspace the irrigating solution, much like a washing machine agitator. Tube 302 may either rotate in one direction or reverse its rotation, like an agitator. The irrigation tube may also act like a suction tube, after the workspace has been irrigated, to remove the agitated, used solution.

In summary, Applicant provides an endodontic instrument whereby the working portion (shaft and cutting head) of the instrument is made from two or more parts rather than a single piece. The component parts may be made of the same material or of different materials. The cutting head portion may be attached to a shaft by means of gluing, welding, soldering or any other reliable means of attaching the two or more parts. Each of the component parts may also be made from one or more parts of the same or different materials.

The cutting head component may be made from one or more parts, solid or hollow from the same or different material. The cutting head may have flutes cut into it. The cutting head may also have ridges (such as diamonds) layered over its surface. The cutting head may have a hole through a portion 11 of or through its entire length for insertion of a shaft or retainer wire.

The noncutting shaft may also be made of one or more parts, solid or hollow from the same or different materials. The noncutting shaft may be made of one part of solid wire, wire mesh, hollow tube, coil, or multi-filar cable. The non cutting shaft may be made of two or more parts such as: a series of gears; an outer part of wire mesh, hollow tube, coil, multi-filar cable and an inner part of solid wire, coil or tube.

Applicant also provides an endodontic instrument whereby the shaft has attached a novel friction grip handle.

Applicant also provides an endodontic instrument whereby a built-in retrieval mechanism is an integral part of the design. Applicants instrument provides that when one or more components fail, all the components, including the failed piece, can be retrieved. Applicant provides an instrument whereby components, including the failed piece, can be retrieved; and whereby components are specifically designed not to fail under the forces imposed by a drive mechanism that is designed to limit the forces it may deliver. Applicants provide dental instruments with a built-in physical retrieval mechanism such that when the instrument fails, pieces of the broken instrument are retrieved as one piece. The retrieval mechanism may consist of a retrieval wire with a boss on the end that is threaded through the shaft and cutting head. The retrieval wire may be stationary or rotate.

Applicants provide an instrument with an early warning mechanism whereby one or more components are designed to fail before another. When the inner or outer portion breaks, it warns the dentist that the instrument should no longer be used. An early warning mechanism may consist of an outer sleeve and an inner core wire. The inner core wire is made of a design such as solid wire and material such as stainless steel that is designed to break before the outer sleeve. The outer sleeve is made of a design and material such as wire mesh, hollow tube, coil, multi-filar cable, such that the outer sleeve will break after the inner core.

Applicant also provides an instrument designed to assist the dentist in cleaning the root canal system by way of injecting and agitating a fluid into the root canal system. The instrument may also inject, agitate and also suction fluid out of the root canal system.

Although the invention has been described with reference to specific embodiments, this description is not meant to be construed in a limiting sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

We claim:

1. An endodontic instrument comprising:

a rotatable shaft having a near end and a removed end, said removed end of said shaft comprising a head cooperating with said shaft so as to rotate therewith;

means for permanently attaching said head to said removed end of said shaft;

a handle portion sized to engage a drive tool, said near end of said shaft being attached to said handle, said longitudinal wire having a near end for attachment to said handle such that said longitudinal wire and said shaft may rotate simultaneously.

said shaft being hollow and having a longitudinally aligned bore therethrough;

a longitudinal wire extending through said longitudinal bore of said shaft and past said head, said longitudinal wire having a stop member at a removed end thereof, said stop member having at least a portion thereof that has a diameter greater than a diameter of said longitudinal bore of said shaft.

2. The endodontic instrument of claim 1, wherein said shaft comprises a semi-rigid coil spring.

3. The endodontic instrument of claim 1, wherein said shaft comprises a first material and said head comprises a second material.

4. The endodontic instrument of claim 1, further comprising a sleeve dimensioned for receipt of said shaft such that said sleeve engages and substantially encloses at least a portion of said shaft.

5. The endodontic instrument of claim 1, wherein said handle further comprises friction grip means.

6. The endodontic instrument of claim 1, wherein said head further comprises grooves or ridges for cutting.

7. The endodontic instrument of claim 1, wherein said shaft further comprises walls defining a plurality of holes for expelling an irrigating solution from said shaft, said near end of said shaft extending beyond said handle and releasably engaging an irrigation solution source.

8. The endodontic instrument of claim 7, wherein said walls of said shaft further comprise one or more low pressure suction holes for retrieving expelled irrigation solution.

9. An endodontic instrument having a handle and a head, and a shaft between the handle and the head, the shaft comprised of a multiplicity of discreet gears, the gears having intermeshing teeth, the gears connecting to the head so as to rotate the head therewith.

* * * * *